United States Patent [19]

Cermak et al.

[11] Patent Number: 5,318,550
[45] Date of Patent: Jun. 7, 1994

[54] URINE COLLECTING APPARATUS

[75] Inventors: Paul Cermak, North Vancouver; Sam Sullivan, Vancouver, both of Canada

[73] Assignee: Tetra Development Society, Vancouver, Canada

[21] Appl. No.: 956,088

[22] Filed: Oct. 2, 1992

[51] Int. Cl.⁵ .............................................. A61F 5/44
[52] U.S. Cl. .................................... 604/349; 604/350; 604/352
[58] Field of Search ................... 604/317–320, 604/323, 332–335, 346, 347, 349–350; 128/761; 4/144.1, 144.2–144.4

[56] References Cited

U.S. PATENT DOCUMENTS

| | | | |
|---|---|---|---|
| 3,339,551 | 9/1967 | Stoutenburgh | 604/349 |
| 3,369,546 | 2/1968 | Hickok | 604/349 |
| 3,421,504 | 1/1969 | Gibbons | 604/349 |
| 3,835,857 | 9/1974 | Rogers, III et al. | 604/349 |
| 3,908,656 | 9/1975 | Binard | 4/144.1 |
| 4,323,067 | 4/1982 | Adams | 604/346 |
| 4,551,141 | 11/1985 | McNeil | 604/317 |
| 4,559,049 | 12/1985 | Haan | 604/350 |
| 4,626,250 | 12/1986 | Schneider | 604/346 |
| 4,713,066 | 12/1987 | Komis | 604/349 |
| 4,713,067 | 12/1987 | Rothenberg et al. | 604/349 |
| 4,740,196 | 4/1988 | Powell | 604/346 |
| 4,846,816 | 7/1989 | Manfredi | 604/349 |
| 4,857,051 | 8/1989 | Larsson | 604/346 |
| 4,889,532 | 12/1989 | Metz et al. | 128/761 |
| 4,994,051 | 12/1991 | Walsh | 604/349 |

FOREIGN PATENT DOCUMENTS

| | | | |
|---|---|---|---|
| 0990166 | 6/1976 | Canada | 604/350 |
| 2279425 | 2/1976 | France | 604/349 |
| 2061731 | 5/1981 | United Kingdom | 604/349 |
| 8201648 | 5/1982 | World Int. Prop. O. | 604/349 |

Primary Examiner—Randall L. Green
Assistant Examiner—Rob Clarke
Attorney, Agent, or Firm—Norman M. Cameron

[57] ABSTRACT

A urine collecting apparatus includes a condom for receiving the penis of a user. A container receives urine from the condom. A conduit extends from the condom to the container. There is a first one-way valve along the conduit which permits a flow of urine from the condom towards the container and prevents a reverse flow of urine towards the condom. There is a resilient squeeze bulb along the conduit between the first one-way valve and the container for pumping urine towards the container when the bulb is squeezed and for providing a suction in the condom when released after squeezing.

3 Claims, 2 Drawing Sheets

URINE COLLECTING APPARATUS

BACKGROUND OF THE INVENTION

1. Field of the Invention

This invention relates to urine collecting apparatuses typically used by disabled persons who do not have adequate bladder control.

2. Description Related Art

Disabled persons who lack adequate bladder control conventionally use a container for receiving urine discharged from the body. For males this apparatus includes a condom for fitting the penis and usually includes a flexible bag which is strapped to the leg. A flexible hose connects the condom to the bag. Such an apparatus is often inconvenient and depends upon gravity to carry the urine from the condom to the container. While it is known to provide a one-way valve on the container to prevent a reverse flow of urine from the container, proper drainage still depends upon gravity and therefore upon the orientation of the person.

Furthermore, persons using such an apparatus having encountered frequent urinary infections. One cause of this is the fact that the penis is continuously in contact with liquid in the condom.

As a consequence, there is a demand for an improved apparatus of the type which reduces the risk of urinary infection and provides a more positive control over flow of urine into the container.

SUMMARY OF THE INVENTION

According to the invention, a urine collecting apparatus includes a condom for receiving the penis of a user. There is a container for receiving urine from the condom. A conduit extends from the condom to the container. There is a first one-way valve along the conduit which permits a flow of urine from the condom towards the container and prevents a reverse flow of urine towards the condom. A resilient squeeze bulb is positioned along the conduit between the first one-way valve and the container for pumping urine towards the container when the bulb is squeezed and for providing a suction in the condom when the bulb is released after squeezing.

The urine collecting apparatus provided by the invention offers significant advantages over the prior art. The discharge of urine into the bag can be accomplished by the patient squeezing the bulb which forces the liquid into the container. Thus the flow of urine is not dependent upon gravity and so the container need not be strapped to the leg of the person as with the prior art. In fact, the container can be positioned above the sheath and the urine can still be discharged into the bag. Furthermore, when the squeeze bulb is released, a suction is applied to the penis in the sheath to remove any remaining liquid and thus keep the penis drier than with prior art appliances of the type. It has been found that this significantly reduces the risk of urinary infection for the user.

DESCRIPTION OF THE PREFERRED EMBODIMENT

Figure 1:
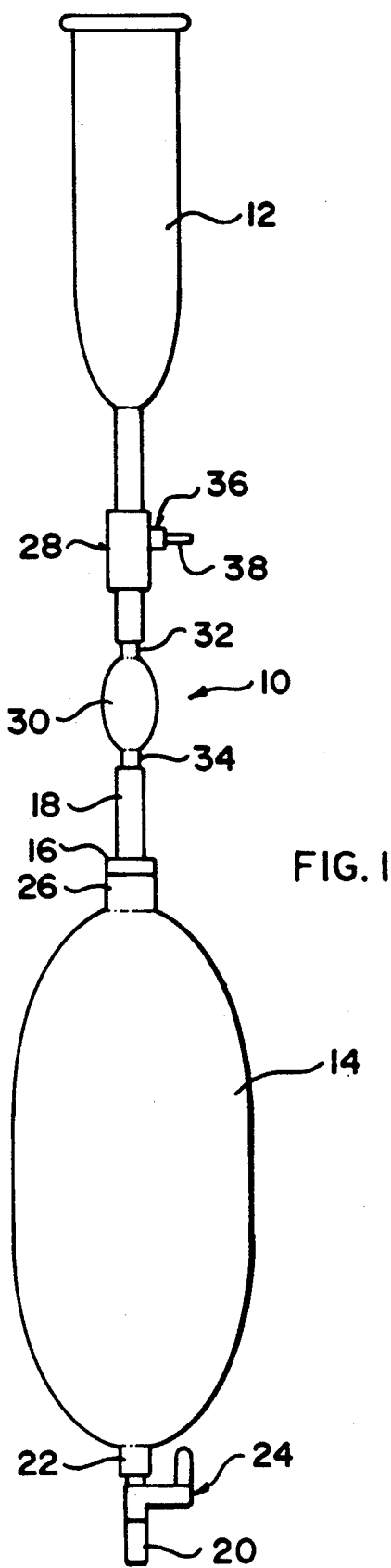
FIG. 1 is a simplified side elevation of a urine collecting apparatus according to an embodiment the invention.

Referring to the drawings, apparatus 10 is used for collecting urine from a male patient lacking adequate bladder control. It includes a condom 12 which is shaped to receive the penis of the patient when in use. This condom is typically a rubber or a synthetic substitute.

A container 14 is used for collecting urine from the patient. In this embodiment, the container is a resilient bag, again of rubber or of similar alternative. This may be similar to the bags previously used with the prior art and strapped to the leg of the patient although this is not critical for the present invention.

The bag has a fitting 16 on top which receives a flexible conduit 18 connected to condom 12. There is a discharge conduit 20 connected to fitting 22 on the bottom of the container which is provided with a manually operated valve 24. The container can be drained by opening valve 24 using lever 25. There is a one-way valve 26 at the top of container 14 which allows urine to drain into container 14, but prevents a reverse flow of liquid from the container to avoid backflow.

As described thus far, apparatus 10 is generally similar to the prior art. However, the apparatus differs from the prior art by including a second one-way valve 28 and a squeeze bulb 30. The squeeze-bulb is located between the second one-way valve 28 and the container 14, while the second one-way valve 28 is located between the squeeze-bulb and condom 12.

The second one-way valve 28 is similar to the first one-way valve 26 already known in the prior art. There is an upper, male threaded valve housing member 29 which threadedly engages a lower, female threaded valve housing member 31. A valve member 43 is located between the housing members. A suitable valve member is commercially available and is sold under the trade mark Little Red Valve. A spiral valve member or others could be substituted. There is a hose connector 33 which connects onto the condom 12 and a hose connector 37 which connects onto bulb 30. However, prior art apparatuses only include one such valve. The valve 28 is oriented to permit a flow of urine from condom 12 into the bulb 30 and towards container 14, but prevents a reverse flow of urine from the bulb 30 towards the condom 12.

The bulb 30 is a simple resilient bulb of rubber or an antibacterial synthetic substitute and is of a type commonly known. It has an opening at a first end 32 which is connected to one-way valve 28 and an opening at a second end 34 which is connected to conduit 18 by tubing 35. When the bulb is squeezed, any urine in the bulb is forced downwardly into the container because one-way valve 28 prevents any flow of fluid in the opposite direction towards the condom. When the bulb is released, one-way valve 26 prevents any flow of urine from the container 14 towards the bulb. However, the suction draws urine from the sheath 12 through one-way valve 28 which is then open.

There is a suction release valve 36 located in the side of one-way valve 28 which is operated by a button 38. The valve is unseated when button 38 is pushed, allowing air to enter the body of valve 28 and thus into the condom 12. This releases the vacuum in the sheath formed when the bulb 30 is released after being squeezed. The resulting suction may cause discomfort to the user, which is alleviated by pushing button 38.

Figure 2:
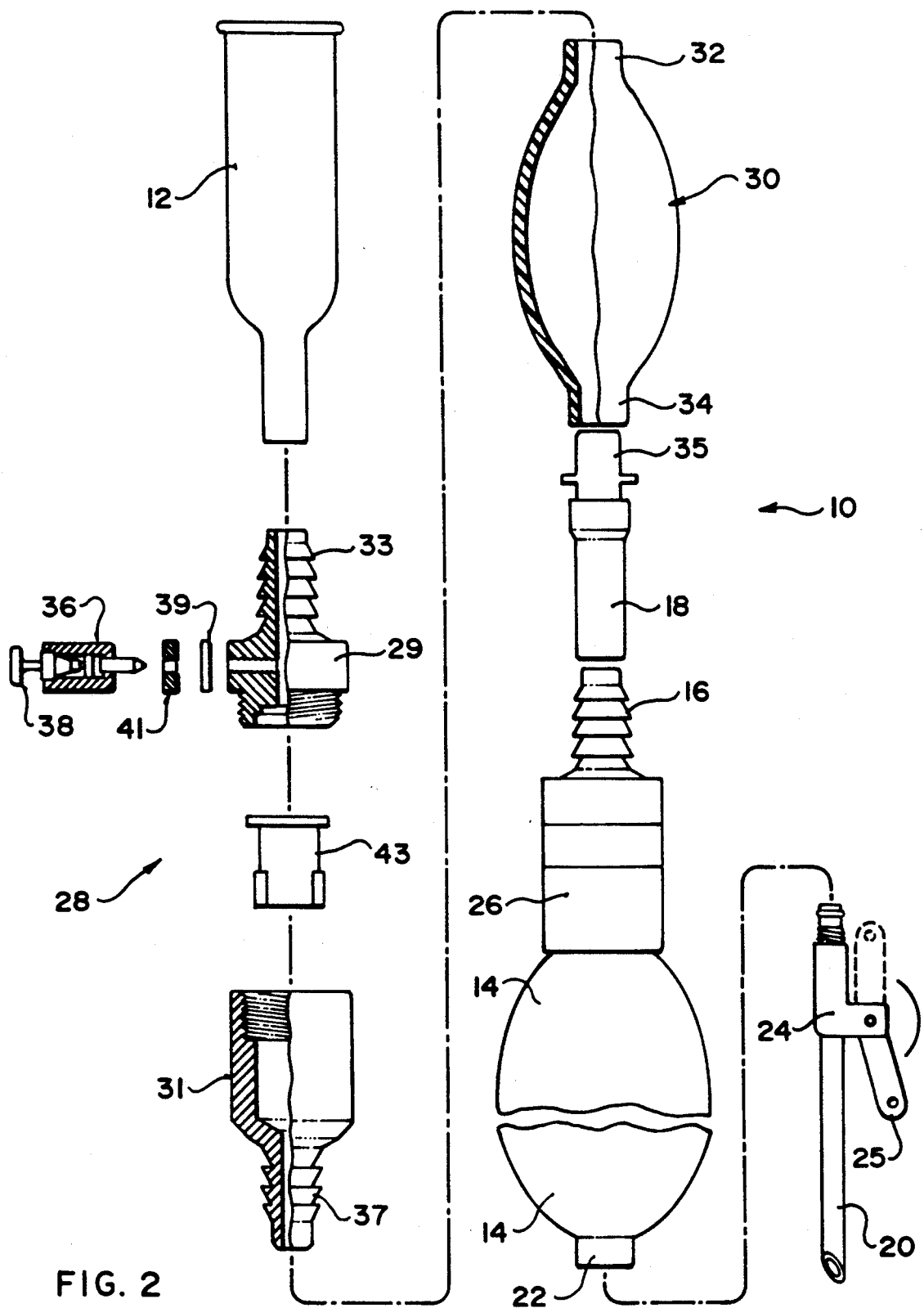
FIG. 2 is an exploded side view thereof which is partly broken away.

Alternatively, as shown in FIG. 2, the release valve 36 may be replaced by a semipermeable membrane 39 held in place by annular member 41. This allows air into the apparatus, but will not allow liquid to leak out.

It will be understood by someone skilled in the art that many of the details provided above are by way of example only and are not intended to limit the scope of the invention defined with reference to the following claims:

What is claimed is:

1. A urine collecting apparatus, comprising:

a condom;

a container for receiving urine from the condom;

a conduit extending from the condom to the container;

first means for permitting a flow of urine from the condom towards the container and preventing a reverse flow of urine towards the condom, said first means including a first one-way valve;

a resilient squeeze bulb along the conduit between the first one-way valve and the container for pumping urine towards the container when the bulb is squeezed and for providing a suction in the condom when released after squeezing;

second means for permitting a flow of urine into the container and preventing a reverse flow of urine towards the bulb from the container, said second means comprising a second one-way valve between the bulb and the container; and third means for selectively releasing suction in the condom including a release valve between the first one-way valve and the condom.

2. An apparatus as claimed in claim 1, wherein the container is a flexible bag.

3. A urine collecting apparatus, comprising:

a condom;

a container for receiving urine from the condom;

a conduit extending from the condom to the container;

first means for permitting a flow of urine from the condom towards the container and preventing a reverse flow of urine towards the condom, said first means including a first one-way valve;

a resilient squeeze bulb along the conduit between the first one-way valve and the container for pumping urine towards the container when the bulb is squeezed and for providing a suction in the condom when released after squeezing;

second means for permitting a flow of urine into the container and preventing a reverse flow of urine towards the bulb from the container, said second means comprising a second one-way valve between the bulb and the container; and third means for selectively releasing suction in the condom including a semipermeable membrane and a valve between the first one-way valve and the condom for allowing air into the apparatus but preventing the leakage of liquids through the membrane.

* * * * *